US009976975B2

(12) United States Patent
Asiri et al.

(10) Patent No.: US 9,976,975 B2
(45) Date of Patent: May 22, 2018

(54) METHOD OF MAKING THIN FILM HUMIDITY SENSORS

(71) Applicant: KING ABDULAZIZ UNIVERSITY, Jeddah (SA)

(72) Inventors: Abdullah Mohamed Asiri, Jeddah (SA); Muhammad Tariq Saeed Chani, Jeddah (SA); Sher Bahadar Khan, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 310 days.

(21) Appl. No.: 14/809,010

(22) Filed: Jul. 24, 2015

(65) Prior Publication Data
US 2017/0023508 A1 Jan. 26, 2017

(51) Int. Cl.
*G01N 27/12* (2006.01)
(52) U.S. Cl.
CPC .................. *G01N 27/121* (2013.01)
(58) Field of Classification Search
None
See application file for complete search history.

(56) References Cited

U.S. PATENT DOCUMENTS

| | | | | |
|---|---|---|---|---|
| 5,252,949 A | * | 10/1993 | Kirby | G01N 33/004 340/632 |
| 5,670,949 A | * | 9/1997 | Kirby | G01N 27/12 340/632 |

(Continued)

FOREIGN PATENT DOCUMENTS

| | | |
|---|---|---|
| JP | 2-57955 | 2/1990 |
| JP | 4-161840 | 6/1992 |

OTHER PUBLICATIONS

Aziz et al., "Characterization of vanadyl phthalocyanine based surface-type capacitive humidity sensors," Journal of Semiconductors, 31(11), 114002-1-114002-6, Nov. 2010.

(Continued)

*Primary Examiner* — Paul West
*Assistant Examiner* — Mark A Shabman
(74) *Attorney, Agent, or Firm* — Richard C. Litman

(57) ABSTRACT

The method of making thin film humidity sensors uses thermal vapor deposition or drop casting techniques to fabricate nickel phthalocyanine-fullerene-based (NiPc-$C_{60}$) quick response humidity sensors with negligible hysteresis. Prior to the deposition of aluminum electrodes, a glass substrate is cleaned by using acetone in an ultrasonic bath for 10 minutes. After cleaning, the substrate is washed with de-ionized water and then dried. A gap is created between two electrodes by masking the glass substrate with copper wire. This assembly is plasma-cleaned for 5 minutes in a thermal evaporator. Subsequently aluminum (Al) thin films are deposited on the assembly. Next, a mixture of equal parts NiPc-$C_{60}$ is deposited onto the gap between the Al electrodes by thermal vapor deposition or by drop casting. A method of forming NiPc-graphene oxide (NiPc-GO) humidity sensors without using instrumentation drop casts an NiPc-GO suspension onto aluminum foil electrodes taped to a substrate.

7 Claims, 17 Drawing Sheets

(56) References Cited

U.S. PATENT DOCUMENTS

| | | | | |
|---|---|---|---|---|
| 6,433,359 B1* | 8/2002 | Kelley | ............... | B82Y 10/00 |
| | | | | 257/40 |
| 6,503,831 B2* | 1/2003 | Speakman | ............... | B41J 2/01 |
| | | | | 257/E27.119 |
| 2005/0053542 A1* | 3/2005 | Harutyunyan | ......... | B82Y 30/00 |
| | | | | 423/447.3 |

OTHER PUBLICATIONS

Berdinsky et al., "Sensor Properties of Fullerence Films and Fullerene Compounds with Iodine," Chemistry for Sustainable Development, 8, 141-146, 2000.

\* cited by examiner

METHOD OF MAKING THIN FILM HUMIDITY SENSORS

BACKGROUND OF THE INVENTION

1. Field of the Invention

The present invention relates to sensors, and particularly to a method of making thin film humidity sensors having application in environmental monitoring, process control, food processing, storage and packaging.

2. Description of the Related Art

Because of the universal existence of water, the control of humidity is very essential, not only for human comfort, but also for manufacturing processes and industrial products. Humidity sensors are widely used in the semiconductor, automobile, medical, pharmaceutical, health care, textile, paper, agriculture and food industries.

Commercially available humidity sensors are fabricated by conventional sensing materials, such as alumina, ceramics, and electrolytic metal oxides. Depending upon the nature of materials, these sensors may be expensive or may require high operational power/temperature and high cost of maintenance. To make the sensor suitable for commercialization, wide range sensitivity, linear response, small hysteresis, short response and recovery time, low cost and low power, along with long-term physical and chemical stability, are the required characteristics. Presently, most of the humidity sensors used in research laboratories and industries are based on water-phase photonic ceramic materials. But, these ceramic-based sensors have problems of response and recovery time and sensitivity towards smoke and dust (contaminants).

Thus, a method of making thin film humidity sensors solving the aforementioned problems is desired.

SUMMARY OF THE INVENTION

The method of making thin film humidity sensors uses various low-cost techniques. Thermal evaporation or drop casting techniques are used to fabricate nickel phthalocyanine-fullerene-based (NiPc-Fullerene or NiPc-$C_{60}$) quick response humidity sensors with negligible hysteresis. Prior to the deposition of aluminum electrodes, a glass substrate is cleaned by using acetone in an ultrasonic bath for 10 minutes. After cleaning, the substrate is washed with de-ionized water and then dried. A gap is created between the two electrodes by masking the glass substrate with copper wire. This assembly is plasma-cleaned for 5 minutes in a thermal evaporator (EDWARD 306). Subsequently aluminum (Al) thin films are deposited on the assembly.

Next, for NiPc-$C_{60}$ composite films, in one method, equal weights (1:1) of both materials are mixed by using mortar and pestle, and the mixture is pressed in the form of a pellet by using a hydraulic press. The pellet is kept in a molybdenum boat under vacuum in the thermal evaporator for thermal vapor deposition of the film. Thin films of 50, 100, and 200 nm are deposited onto the gap between the preliminary deposited Al electrodes. In another method, the film is deposited on the aluminum electrodes by drop casting. A method of forming NiPc-graphene oxide (NiPc-GO) humidity sensors without using instrumentation is also described.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
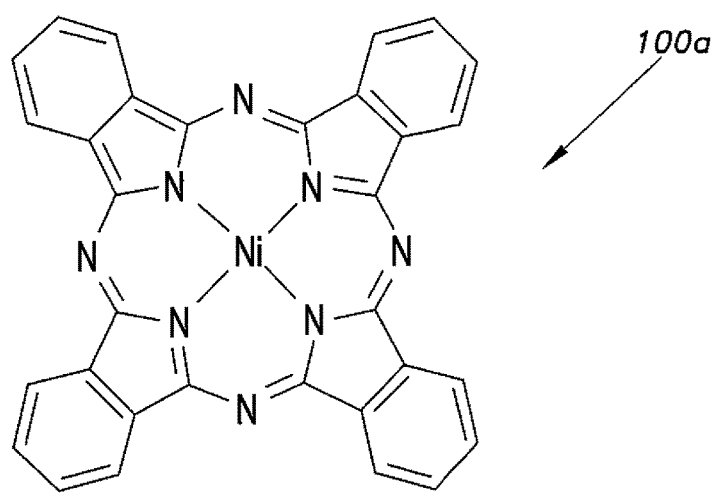
FIG. 1A is the molecular structure of nickel phthalocyanine.
Figure 1B:
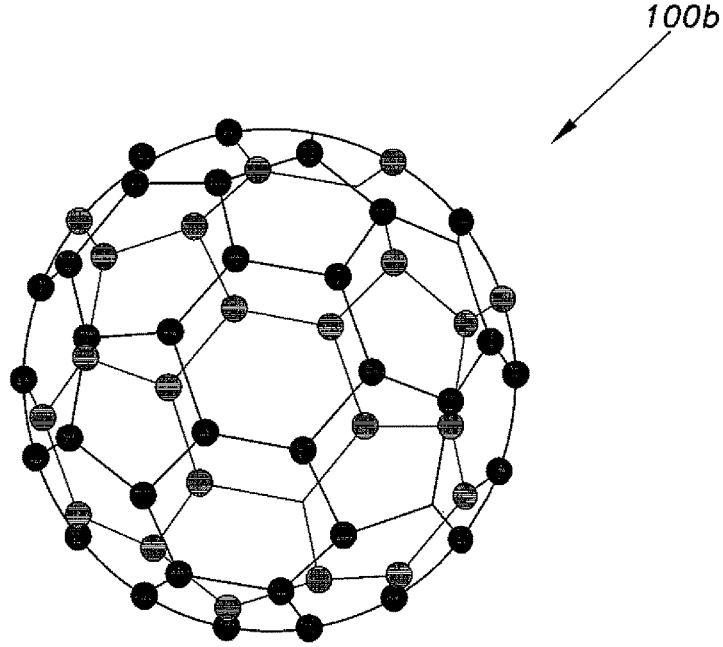
FIG. 1B is a diagram showing the molecular structure of fullerene.
Figure 2A:
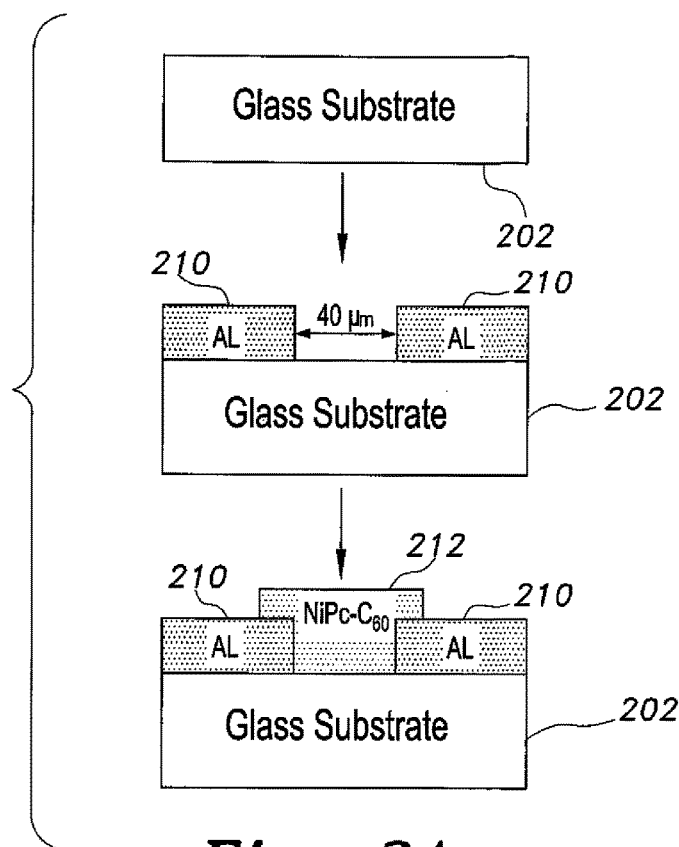
FIG. 2A is a diagram graphically illustrating steps in the method of making NiPc-$C_{60}$ thin film humidity sensors according to the present invention.

The method of making thin film humidity sensors uses various low cost techniques. The thermal evaporation or drop casting techniques are used to fabricate NiPc-Fullerene based quick response humidity sensors with negligible hysteresis. FIG. 1A shows the molecular structure of NiPc (nickel phthalocyanine) 100a. FIG. 1B shows the molecular structure of C$_{60}$ (Fullerene) 100b. The fabrication process is shown in FIG. 2A. Prior to the deposition of aluminum electrodes, a glass substrate 202 is cleaned by using acetone in an ultrasonic bath for 10 minutes. After cleaning, the substrate 202 is washed with de-ionized water and then dried. A gap is created between two electrodes by masking the glass substrate with copper wire. This assembly is plasma-cleaned for 5 minutes in a thermal evaporator (EDWARD 306). Subsequently aluminum (Al) thin films 210 are deposited on the assembly.

Next, for thermal vapor deposition of NiPc-C$_{60}$ composite films 212, equal weights (1:1) of both materials (NiPc and fullerene) are mixed by using mortar and pestle, and the mixture is pressed in the form of a pellet by using a hydraulic press. The pellet is kept in a molybdenum boat of the vacuum thermal evaporator. Thin films of 50, 100 and 200 nm thickness are deposited onto the gap between the Al electrodes 210. The previously deposited Al electrodes 210 are 10×5 mm in dimension.

Figure 2B:
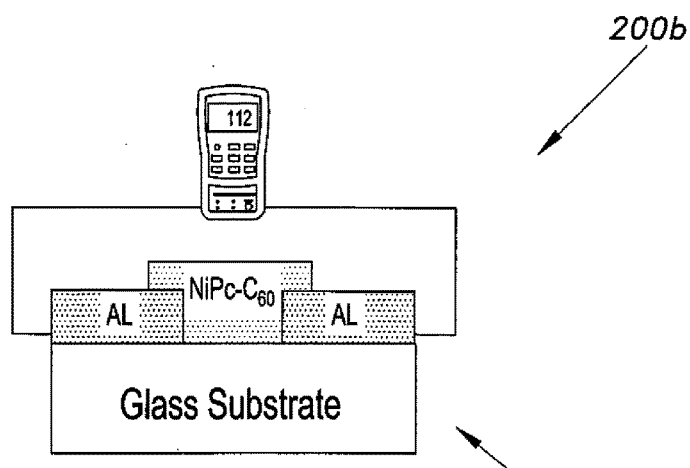
FIG. 2B is a schematic diagram showing a NiPc-$C_{60}$ thin film humidity sensor according to the present invention.

During the deposition, the vacuum is maintained at 1.6× 10$^{-5}$ mbar and the rate of deposition is 0.1-0.2 nm/sec, while the substrates are held at room temperature. The rate of deposition is controlled, and the thickness is monitored by crystal thickness monitor FTM5. FIGS. 2A and 2B show the schematic illustration of the fabrication process and the completed humidity sensor 200b, respectively. These sensors were tested using circuit 290 with the films in an "as fabricated" condition and after annealing the thin films at 100° C. in air for one hour.

In an alternative procedure, the NiPc-C$_{60}$ films 212 are deposited by drop casting on the preliminarily deposited electrodes 210 (5×5 mm). The equal weights of NiPc and C$_{60}$ (fullerene) are dissolved in dichlorobenzene. The solution is deposited into the gap between the two electrodes 210 and the solvent evaporates to form nanocomposite films of 20 μm thickness.

Figure 3A:
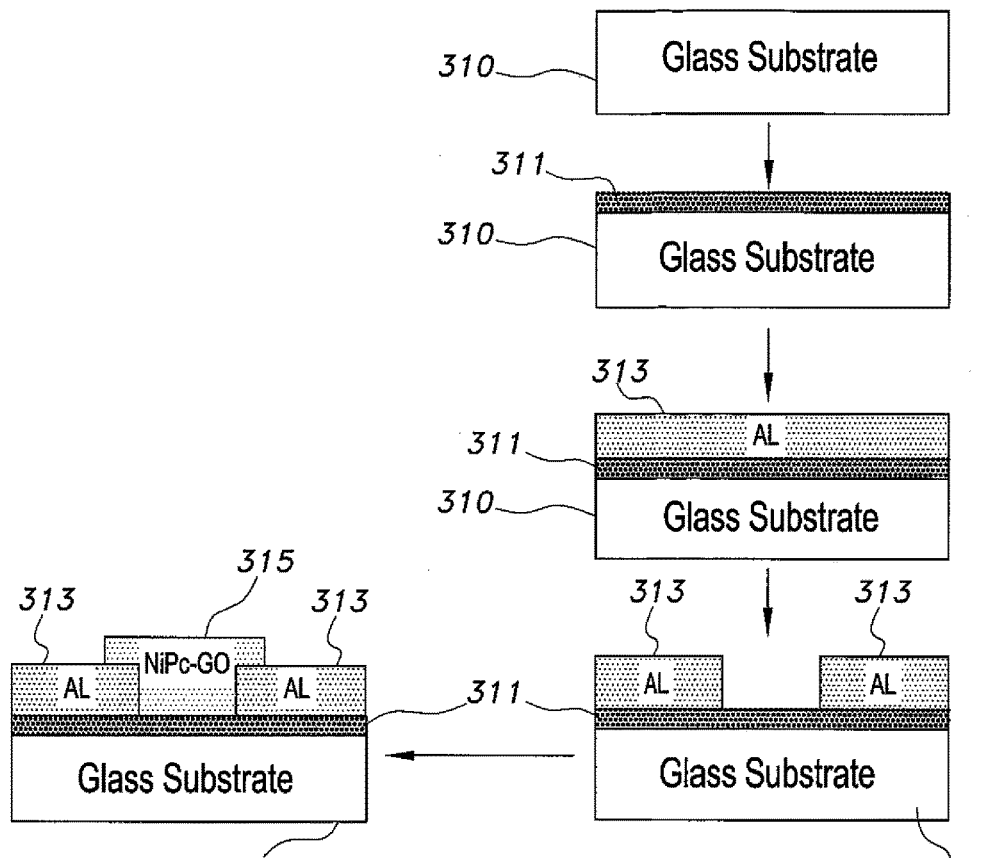
FIG. 3A is a diagram graphically illustrating steps in the method of making NiPc-GO thin film humidity sensors according to the present invention.
Figure 3B:
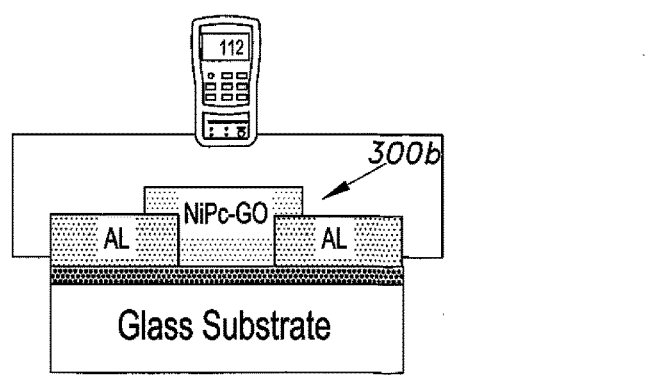
FIG. 3B is a schematic diagram showing a NiPc-GO thin film humidity sensor according to the present invention.

In yet another procedure 300a, as shown in FIG. 3A, a nickel phthalocyanine-graphene oxide (NiPc-GO) humidity sensor comprising NiPc-GO nanocomposite films 315 deposited onto aluminum electrodes 313 fixed on a glass substrate 310 is fabricated using instrument-less technology. Glass slides are used as a substrate, and aluminum foil is used as an electrode, fixed on the substrate by using double-sided adhesive tape 311. A gap of 40 μm forms two electrodes made from the aluminum 313, the size of each electrode being 5×5 mm. The equal amounts (1:1) of NiPc and GO are dissolved and dispersed, respectively, in 2.5 ml of ethanol and 20-50 μm thick films are deposited by drop casting. FIG. 3A graphically illustrates the fabrication process. In FIG. 3B, the completed Al/NiPc-GO/Al humidity sensor 300b is shown in test circuit 390.

The testing of the sensors was done by using a testing setup, which was indigenously made by our device testing laboratory. It consists of a testing chamber, water chamber, gas hoses, low pressure gauges, humidity meters and inductive-capacitive-resistance (LCR) meters. To create the humidity in the testing chamber, nitrogen gas is passed through water, and is then injected in to the chamber. The humidity is measured with the accuracy of ±1.5% by using Traceable Humidity and Temperature meter Model 4085 (Control Company, USA). The capacitance and dissipation are measured at different frequencies by using LCR meter Agilent U1733C. The following expression is used for the calculation of resistance (R), $$R=1/(2\pi f C D), \quad (1)$$

where f, C and D are frequency, capacitance and dissipation, respectively. The surface morphology of the NiPc-C$_{60}$ thin films in as-fabricated and annealed form were investigated by field emission scanning electron microscope (FESEM). The porous surface of the film in as-fabricated form was found to be well developed, with grain sizes in the range of 80-200 nm. This porosity endorses the diffusion of water molecules and enhances the electrical response to the humidity.

Figure 4A:
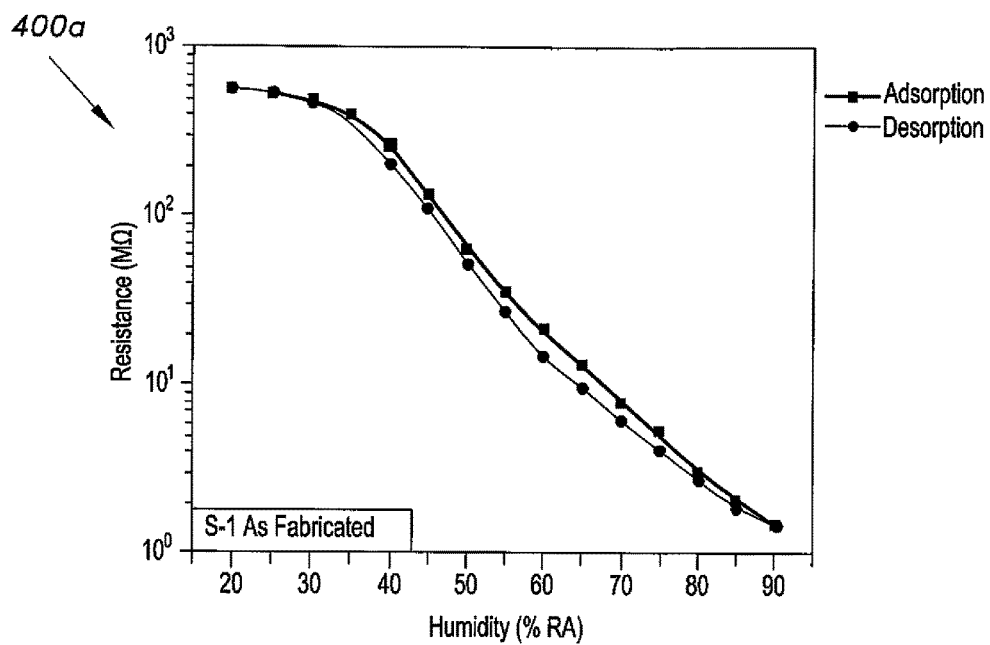
FIG. 4A is a plot showing resistance-humidity relationship and adsorption-desorption behavior of the NiPc-$C_{60}$ nanocomposite sensors prepared by thermal vapor deposition with 50 nm film thickness, as fabricated, measured at 100 Hz.
Figure 5A:
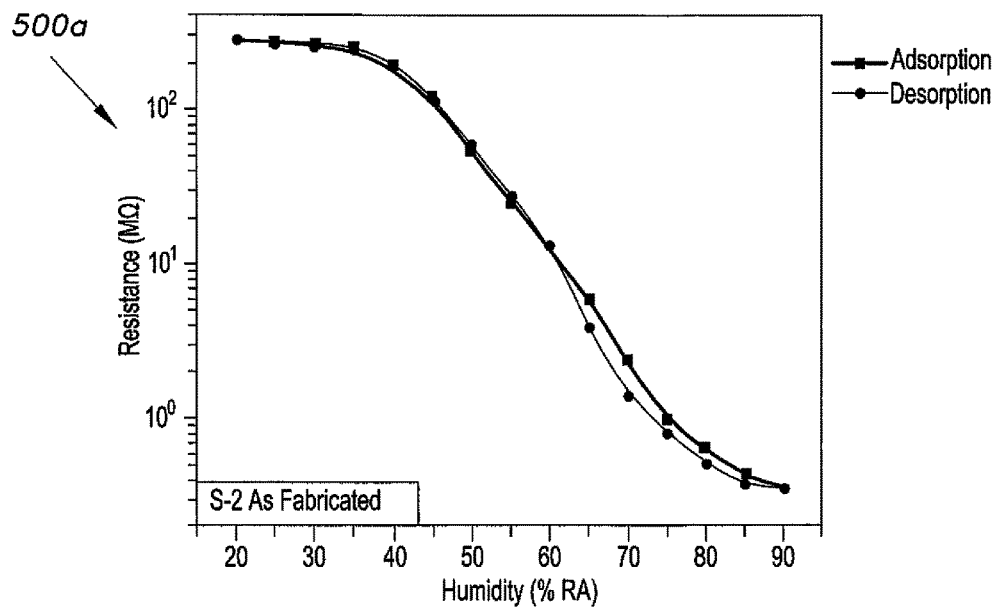
FIG. 5A is a plot showing resistance-humidity relationship and adsorption-desorption behavior of the NiPc-$C_{60}$ nanocomposite sensors prepared by thermal vapor deposition with 100 nm film thickness, as fabricated, measured at 100 Hz.
Figure 5B:
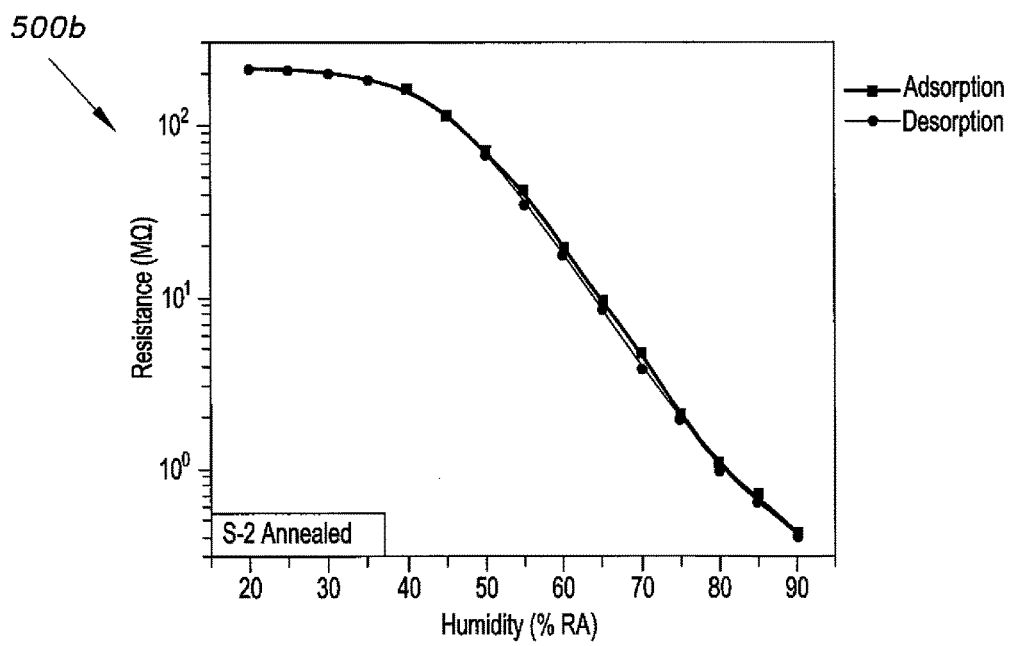
FIG. 5B is a plot showing resistance-humidity relationship and adsorption-desorption behavior of the NiPc-$C_{60}$ nanocomposite sensors prepared by thermal vapor deposition with 100 nm film thickness after being annealed, measured at 100 Hz.
Figure 5C:
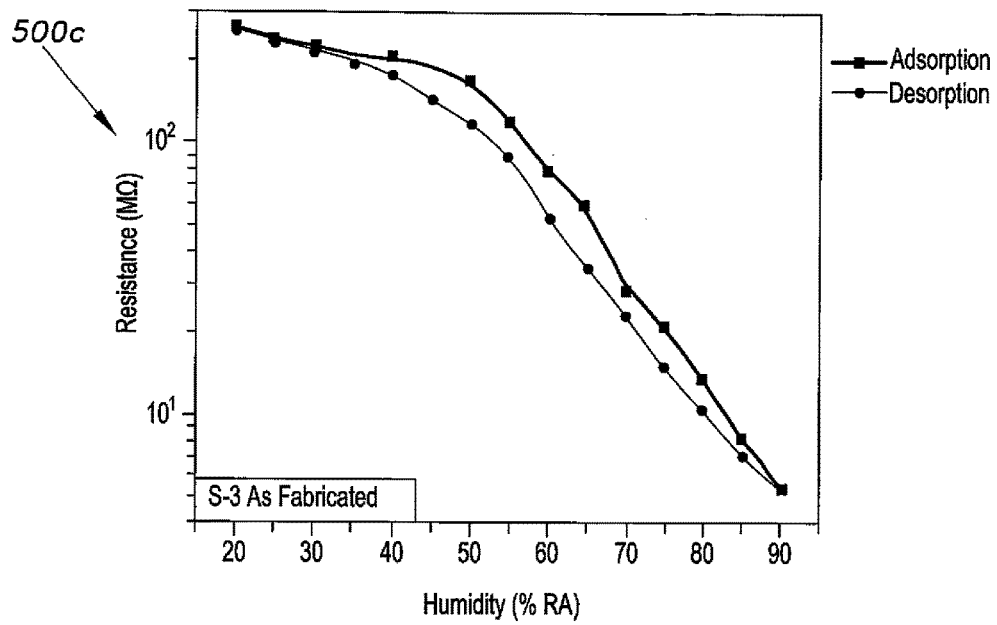
FIG. 5C is a plot showing resistance-humidity relationship and adsorption-desorption behavior of the NiPc-$C_{60}$ nanocomposite sensors prepared by thermal vapor deposition with 200 nm film thickness, as fabricated, measured at 100 Hz.

Plots 400a, 500a, and 500c of FIGS. 4A, 5A and 5C, respectively, show the resistance-humidity relationships of the Al/NiPc-C$_{60}$/Al sensors prepared by thermal vapor deposition with different film thicknesses (50, 100, and 200 nm) measured at 100 Hz during adsorption and desorption processes on a semi-logarithmic scale. It can be seen that the resistance shows enormous decrease in the intervals of 20-90% RH. The resistance decreases with increase in humidity and vice versa. The resistance humidity behavior shows considerable hysteresis in the interval of 40-85% RH. The average sensitivity (change in resistance) of the sensors having 50-200 nm thick NiPc-C$_{60}$ films is 8.17×10$^3$ to 3.74×10$^3$ kΩ/% RH at a frequency of 100 Hz. The average sensitivity decreases with increase in thickness of the films, and also with increase in frequency. The change in resistance of NiPc-C$_{60}$ due to change in humidity may be attributable to adsorption (chemisorption and physisorption) and absorption of water molecules firstly and secondly to increase of charges concentration because of doping of NiPc-C$_{60}$ and formation of charge transfer complexes. With respect to Co-polyaniline nanocomposite thin films, these mechanisms have been described in prior investigations by other artisans having ordinary skill.

Water is famous for its protonation, which starts by the electrolysis of water on anode and cathode, and interaction takes place between protons and conjugated double bonds of organic materials. As a dopant, water plays a crucial role in the conductivity of H$^+$ ions from anode to cathode through the organic film, and it increases the mobility by reducing the interaction between $H^+$ ions and polar groups of organic material. The higher sensitivity of thin (50 nm) film as compared to thick (200 nm) film is attributed to the higher concentration of water molecules due to diffusion. The adsorption and desorption processes are repeatable, and depend on doping and dedoping of the organic film, along with other concerned processes. The hysteresis may appear firstly due to difference in rate of doping and dedoping processes, and secondly due to difference in adsorption and desorption rate of water vapors. The nature of film porosity may be another reason for hysteresis, which makes adsorption easier because of capillary effect and large surface area, while it provides hindrance in desorption.

Figure 6:
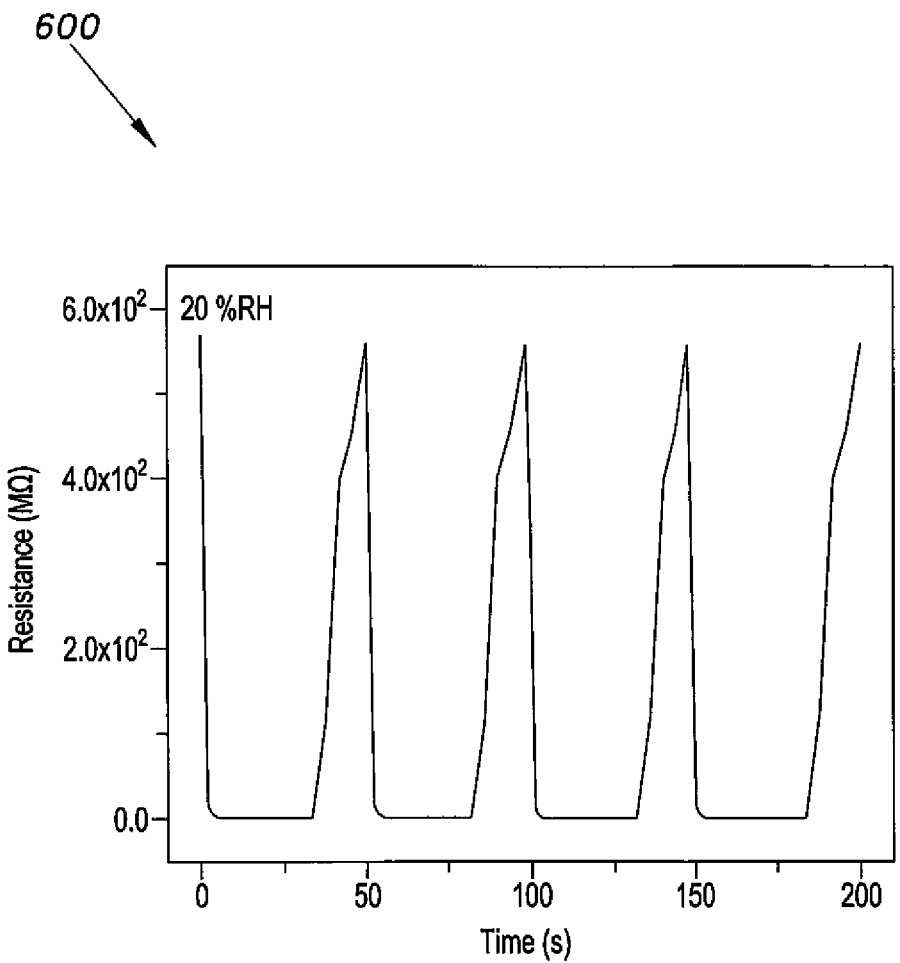
FIG. 6 is a plot showing response and recovery times of the NiPc-$C_{60}$ nanocomposite sensor prepared by thermal vapor deposition in an as-fabricated state according to the present invention.

The response and recovery times ($\tau_{res}$ and $\tau_{rec}$) are also measured, which are the time taken by the sensor to measure 90% of the total resistance change. The response ($\tau_{res}$) and recovery ($\tau_{rec}$) times of the sensors are measured by suddenly changing humidity from 20 to 90% RH and from 90 to 20% RH, respectively. The humidity testing setup used in this work contains a testing chamber, which consists of two sections (small and large) separated by a window. Each section in the chamber has inlet and outlet valves, and the window can be opened or closed manually. In small section, there is a sample holder, where we put the sensor, and for sudden exposure of the sensor to higher or lower humidity, first we maintain required humidity level in the large chamber, and then open the window. For 50 nm thick sensors, the response and recovery times are 4 sec and 16 sec, respectively. Plot 600 of FIG. 6 shows the response recovery behavior of a sensor having 50 nm thick NiPc-$C_{60}$ films. The reasons for the delay in recovery time may be the same as for hysteresis.

Figure 4B:
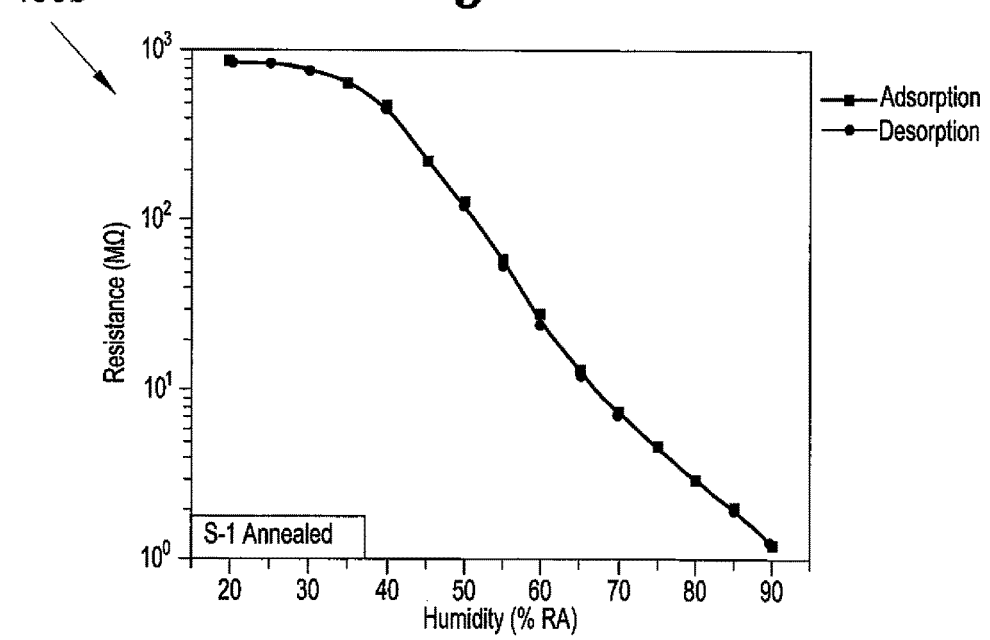
FIG. 4B is a plot showing resistance-humidity relationship and adsorption-desorption behavior of the NiPc-$C_{60}$ nanocomposite sensors prepared by thermal vapor deposition with 50 nm film thickness after being annealed, measured at 100 Hz.
Figure 5D:
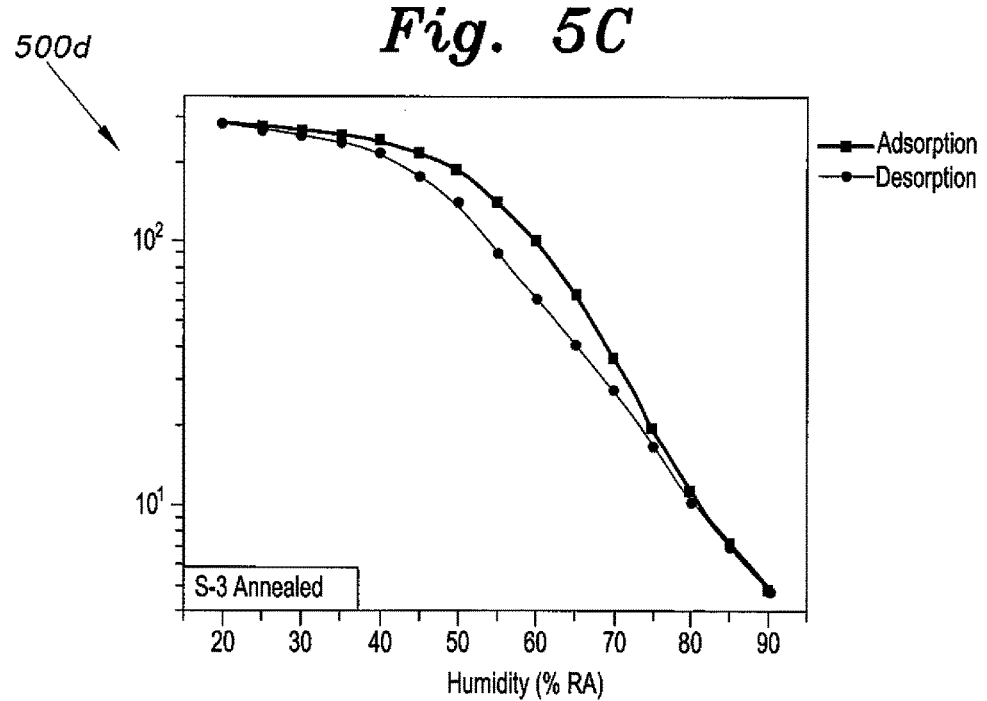
FIG. 5D is a plot showing resistance-humidity relationship and adsorption-desorption behavior of the NiPc-$C_{60}$ nanocomposite sensors prepared by thermal vapor deposition with 200 nm film thickness after being annealed, measured at 100 Hz.

Post deposition annealing re-organizes the sensor's structure, thereby creating very useful long-term stability of the sensors. The fabricated samples are also annealed at 100° C. for 1 hour. After annealing, samples are tested for humidity sensing. The resistance humidity relationships of annealed samples are shown in plots 400*b*, 500*b*, and 500*d* of FIGS. 4B, 5B, and 5D, respectively. From these drawings, it can be observed that the overall resistance of the sensors increases and the hysteresis decreases significantly, which can be attributed to the change in the morphology and the porous formation of the NiPc-$C_{60}$ films. The change in morphology and porosity of the film as a result of annealing can be observed in the FESEM images. The overall changes in the resistance (sensitivity) of the sensors fabricated by physical vapor deposition (PVD) upon changing humidity from 20% to 90% RH are given in Table 1.

Figure 7:
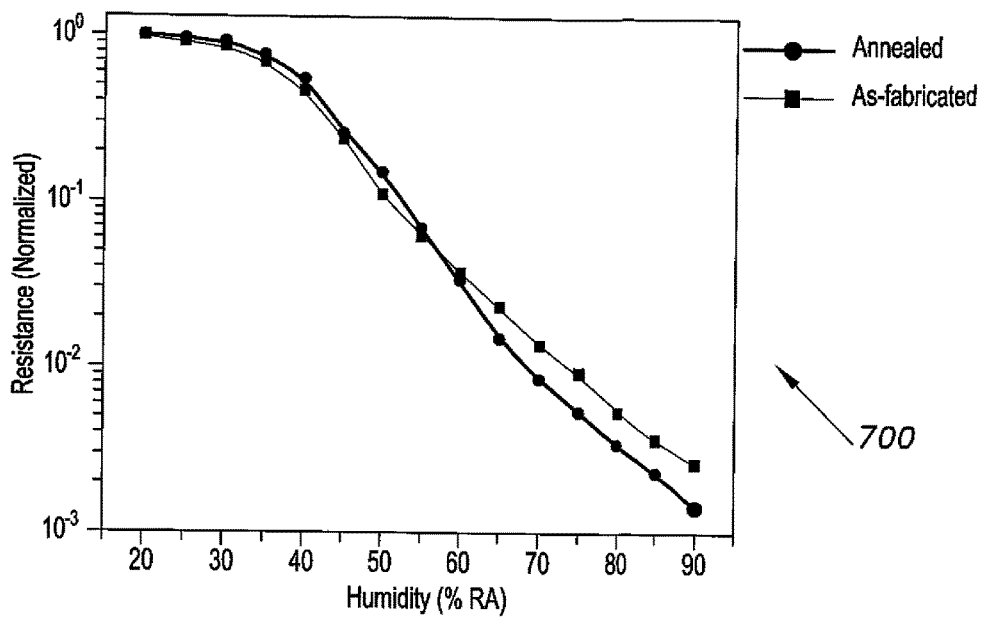
FIG. 7 is a plot showing the effect of annealing at 100° C. on the resistance-humidity relationship of NiPc-$C_{60}$ nanocomposite sensors prepared by thermal vapor deposition.
Figure 8:
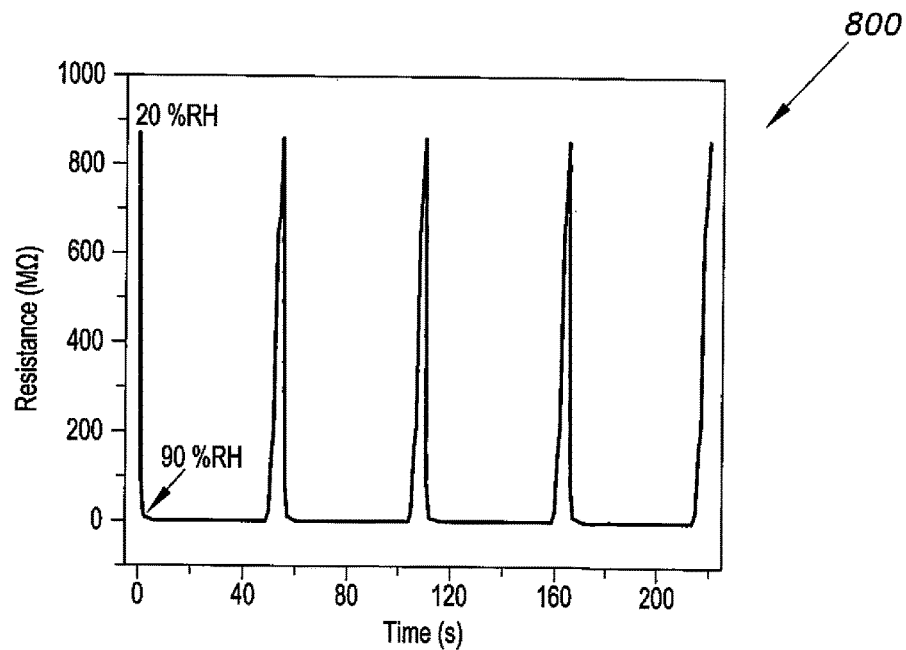
FIG. 8 is a plot showing the response and recovery times of the 50 nm thick NiPc-nanocomposite humidity sensor prepared by thermal vapor deposition after annealing at 100° C.

The sensitivity of the sensors increases on average 30% and 27% respectively for 50 nm and 200 nm thick sensors. The comparison of resistance-humidity relationship is given in plot 700 of FIG. 7. It is also observed that annealing results in reduction of response and recovery time up to 75% and 69%, respectively. After annealing the response ($\tau_{res}$) and recovery ($\tau_{rec}$) times were 1 sec and 5 sec, respectively. Plot 800 of FIG. 8 shows the effect of annealing on response and recovery times of sensors with 50 nm thick NiPc-$C_{60}$ film.

Figure 9:
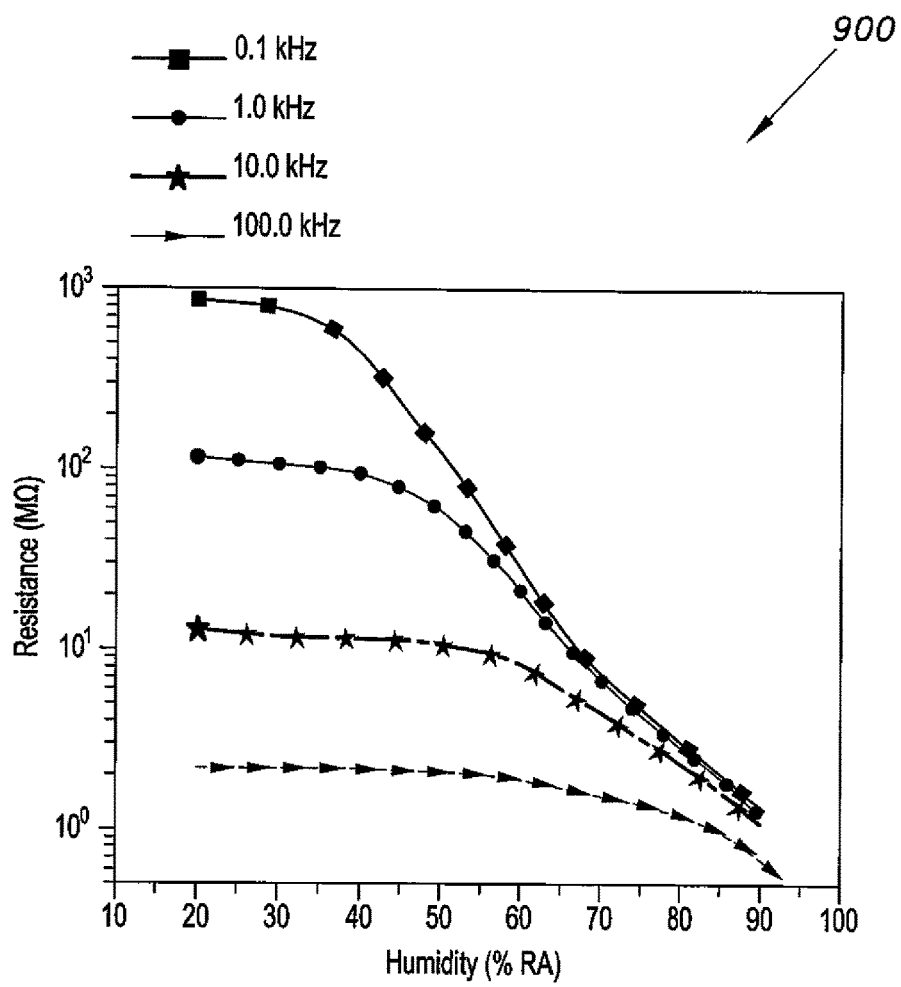
FIG. 9 is a plot showing the resistance-humidity relationship of the NiPc-$C_{60}$ nanocomposite sensor prepared by thermal vapor deposition at various frequencies.

With the increase in frequency, the resistance decreases at any humidity level, and the effect of frequency is prominent throughout the humidity range (20-90% RH), as shown in plot 900 of FIG. 9. The dependence of the resistance on the frequency can be explained by the dependence of dielectric permittivity, mobility of ions (firstly) and electrons (secondly) and transit time of charges transfer on the frequency. The results also reveal that with increase in frequency, the average sensitivity of the sensors decreases, which may be attributable to comparability of the relaxation time of the related processes with period of applied measuring AC voltage.

Figure 10A:
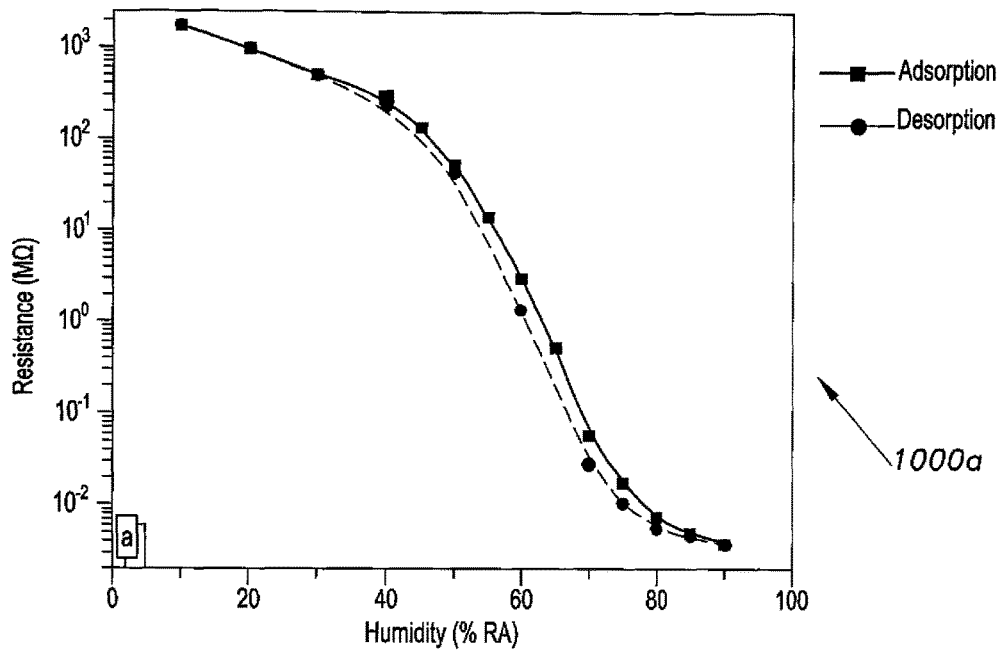
FIG. 10A is a plot showing the resistance-humidity relationships and adsorption-desorption behavior of the NiPc-$C_{60}$ nanocomposite sensors with 20 μm thick drop-casted film before annealing.
Figure 10B:
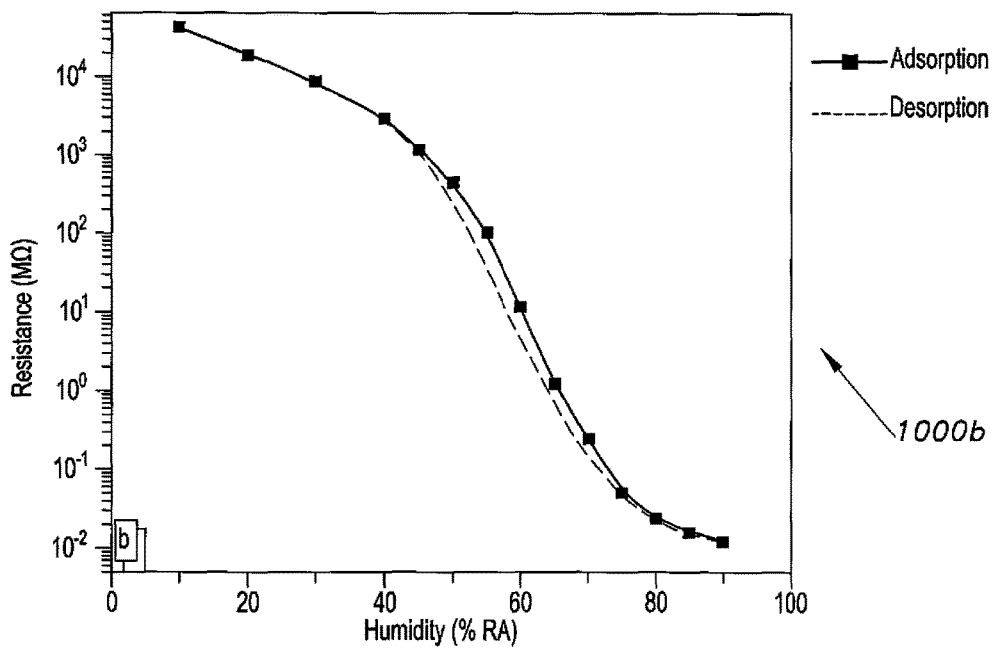
FIG. 10B is a plot showing the resistance-humidity relationships and adsorption-desorption behavior of the NiPc-$C_{60}$ nanocomposite sensors with 20 μm thick drop-casted film after annealing at 100° C.
Figure 11:
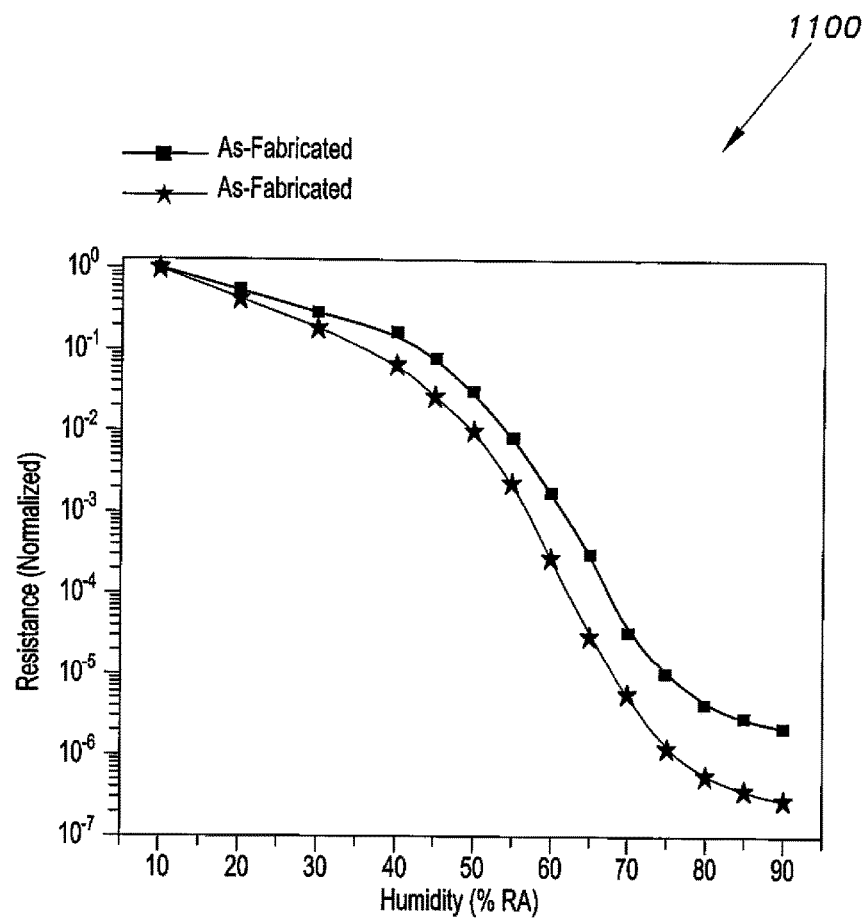
FIG. 11 is a plot showing the effect of annealing on the resistance-humidity relationship of NiPc-$C_{60}$ nanocomposite based drop-casted sensors.
Figure 12:
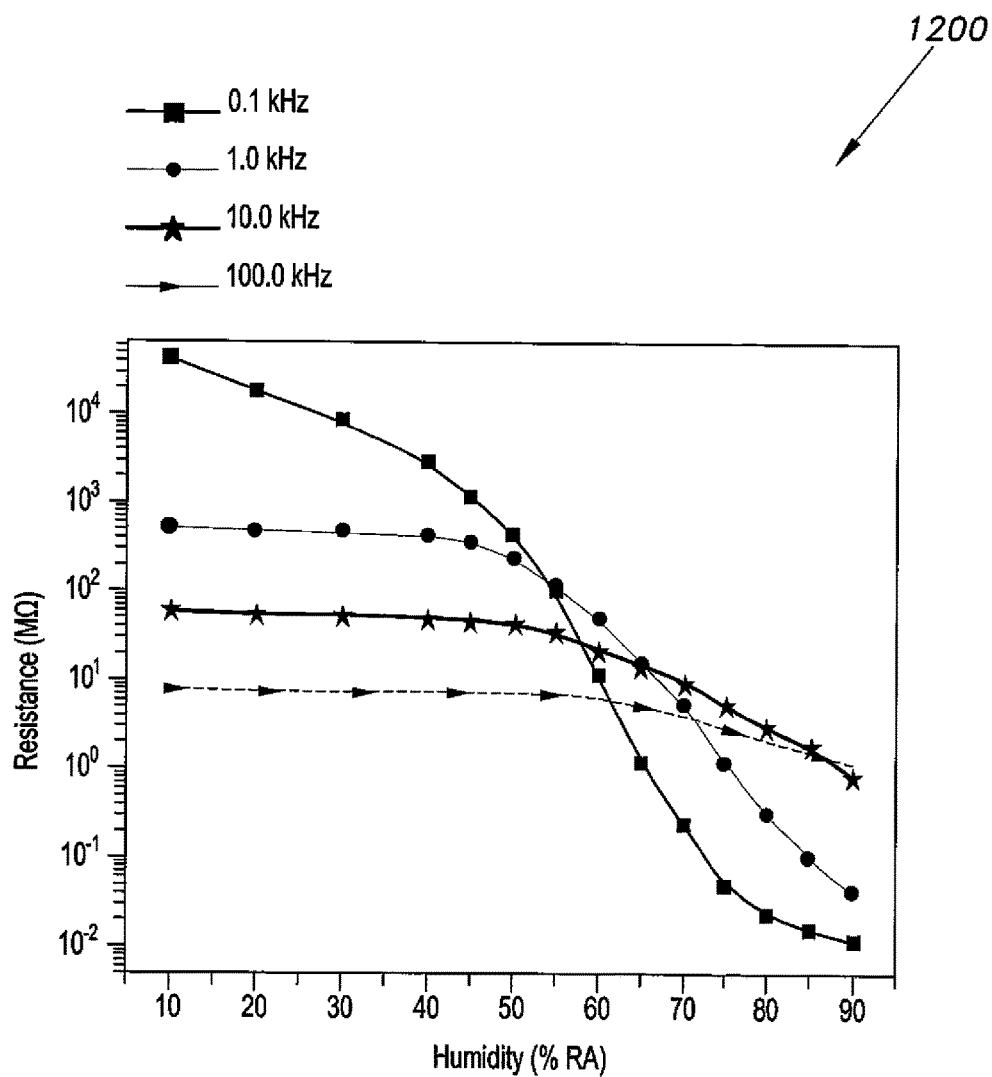
FIG. 12 is a plot showing the effect of frequency on resistance-humidity relationship of the NiPc-C$_{60}$ nanocomposite based sensor prepared by drop casting.
Figure 13:
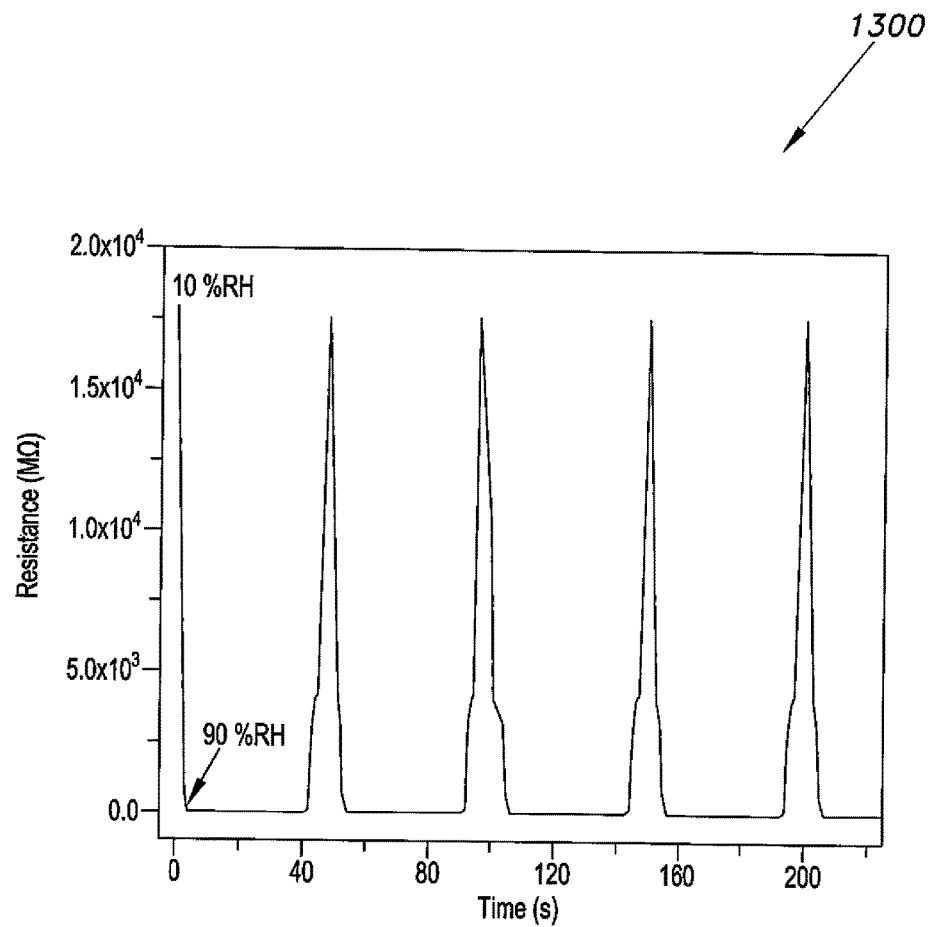
FIG. 13 is a plot showing the response and recovery times of the NiPc-C$_{60}$ nanocomposite based drop-casted sensors after annealing at 100° C. for 1 hr.

The resistance-humidity relationships of the NiPc-$C_{60}$ humidity sensors prepared by drop casting at 100 Hz during adsorption and desorption process on semi-logarithmic scale are shown in FIGS. 10A and 10B. The sensors with 20 μm thick film show high sensitivity (212×10³ kΩ/% RH) in as-fabricated condition (plot 1000*a* of FIG. 10A), which increases up to 530×10³ kΩ/% RH (plot 1000*b* of FIG. 10B) as a result of annealing at 100° C. It is also evident from FIG. 10B that the annealing increases the overall sensitivity of the sensor, with negligible hysteresis. The comparison of resistance-humidity relationship is given in plot 1100 of FIG. 11. Like thermally evaporated films, the initial resistance of the sensor decreases with increase in frequency (plot 1200 of FIG. 12). The possible reasons for this type of behavior are given in previous sections. In the annealed condition, the response and recovery times of the sensors were measured and found to be 4 s and 6 s, respectively. The response and recovery behavior of the sensors is shown in plot 1300 of FIG. 13, which is far better than the commercially available humidity sensors.

The high sensitivity of the NiPc-$C_{60}$ to humidity is first of all due to high diffusivity of the water molecules in to the NiPc-$C_{60}$ thin films. Secondly, it is due to molecular interactions between water molecules and NiPc-$C_{60}$, which results in the formation of charge-transfer complexes and, accordingly, the increase in concentration of the charge carriers as electrons and holes.

Figure 14:
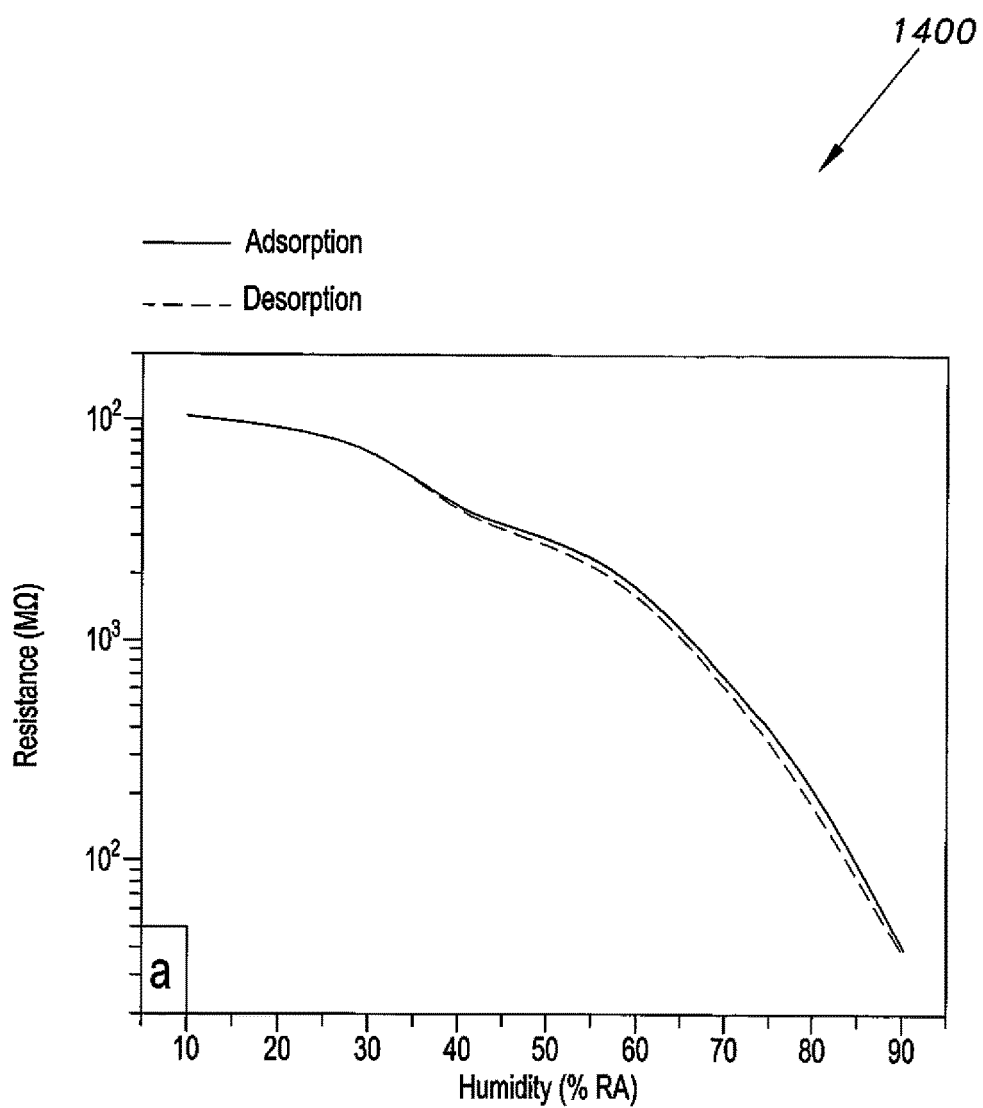
FIG. 14 is a plot showing the resistance-humidity relationships and adsorption-desorption behavior of the NiPc-GO nanocomposite sensors fabricated by using instrument-less technique according to the present invention.

The resistance-humidity relationships of the NiPc-GO humidity sensors prepared by using instrument-less technology at 100 Hz during adsorption and desorption process on semi-logarithmic scale are shown in plot 1400 of FIG. 14. With increase in humidity the resistance decreases, which may be attributable firstly to the absorption and adsorption

TABLE 1

| Film type Thickness | Thermal vapor evaporation | | | | Drop cast |
|---|---|---|---|---|---|
| Frequency | 50 nm | | 200 nm | | 20 μm |
| (KHz) | As fabricated | Annealed | As fabricated | Annealed | Annealed |
| 0.1 | $8.17 \times 10^3$ | $12.34 \times 10^3$ | $3.74 \times 10^3$ | $3.93 \times 10^3$ | $530.5 \times 10^3$ |
| 1.0 | $1.25 \times 10^3$ | $1.64 \times 10^3$ | $1.06 \times 10^3$ | $1.17 \times 10^3$ | $6.60 \times 10^3$ |
| 10 | $1.35 \times 10^2$ | $1.70 \times 10^2$ | $1.01 \times 10^2$ | $1.74 \times 10^2$ | $7.34 \times 10^2$ |
| 100 | $1.98 \times 10^1$ | $2.17 \times 10^1$ | $0.96 \times 10^1$ | $1.16 \times 10^1$ | $8.30 \times 10^1$ |

Humidity Sensitivity (KΩ/% RH) of the Sensors of water molecules, and secondly, to the increase of charges concentration due to the doping of NiPc-Go and formation of charge transfer complexes. The sensors with 20 μm and 35 μm thick NiPc-GO films show no hysteresis, while the sensor with 50 μm thick film has very small hysteresis. The average sensitivity of the sensors having 20-50 μm thick NiPc-GO films is $130 \times 10^3$ kΩ/% RH to $19.8 \times 10^3$ kΩ/% RH in as-fabricated condition (detail is given in Table 2).

TABLE 2

Humidity Sensitivity (KΩ/% RH) Of The NiPc-GO Sensors

| Frequency (KHz) | NiPc-GO Thickness (μm) | | |
|---|---|---|---|
| | 20 | 35 | 50 |
| 0.1 | $130.4 \times 10^3$ | $28.55 \times 10^3$ | $19.81 \times 10^3$ |
| 1.0 | $8.22 \times 10^3$ | $4.26 \times 10^3$ | $4.13 \times 10^3$ |
| 10 | $7.0 \times 10^2$ | $5.72 \times 10^2$ | $7.67 \times 10^2$ |
| 100 | $3.42 \times 10^1$ | $7.24 \times 10^1$ | $1.17 \times 10^2$ |

Figure 15:
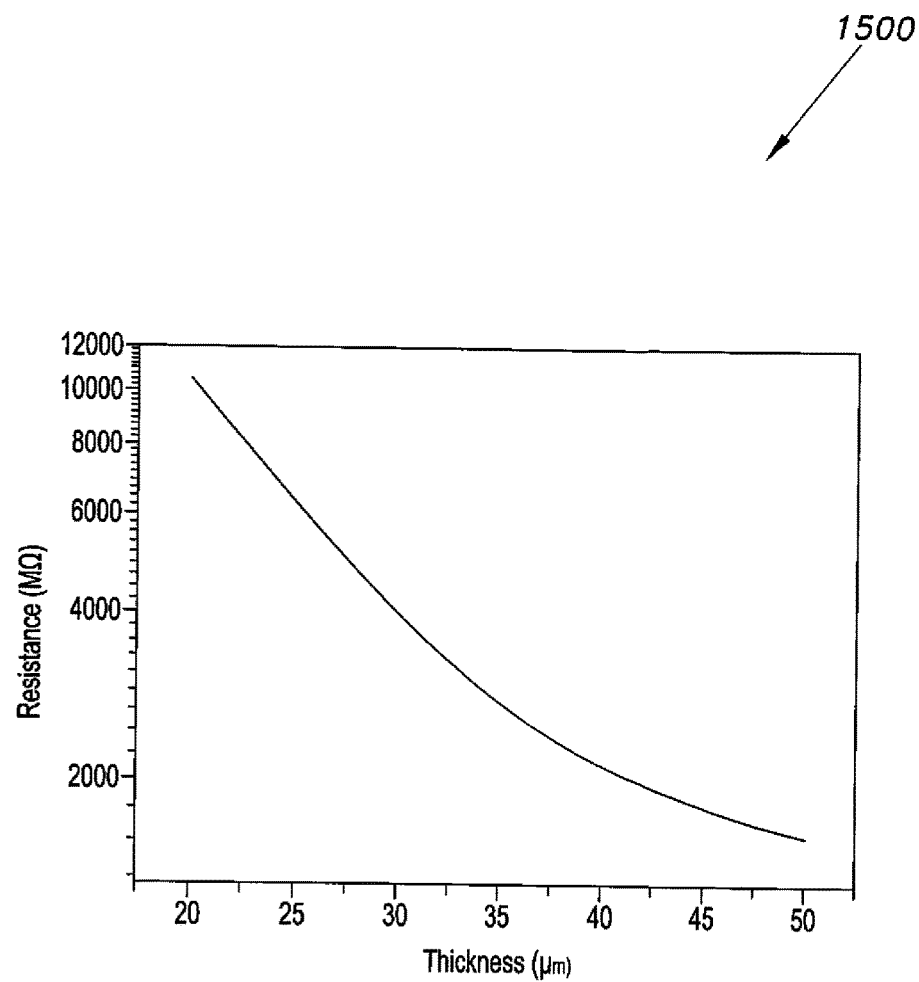
FIG. 15 is a plot showing the resistance-thickness relationship of the NiPc-GO nanocomposite sensors.
Figure 16:
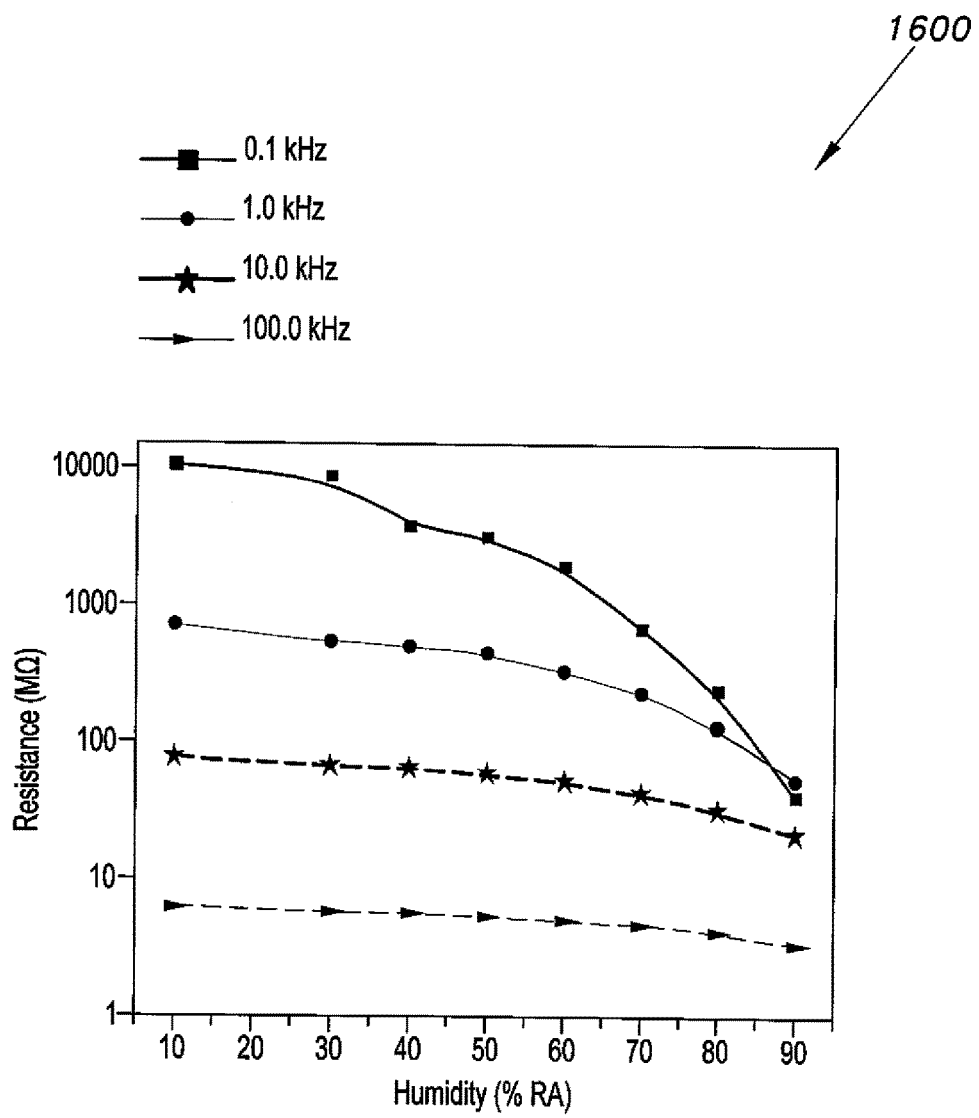
FIG. 16 is a plot showing the effect of frequency on the resistance-humidity relationship of the NiPc-GO nanocomposite-based humidity sensor.
Figure 17:
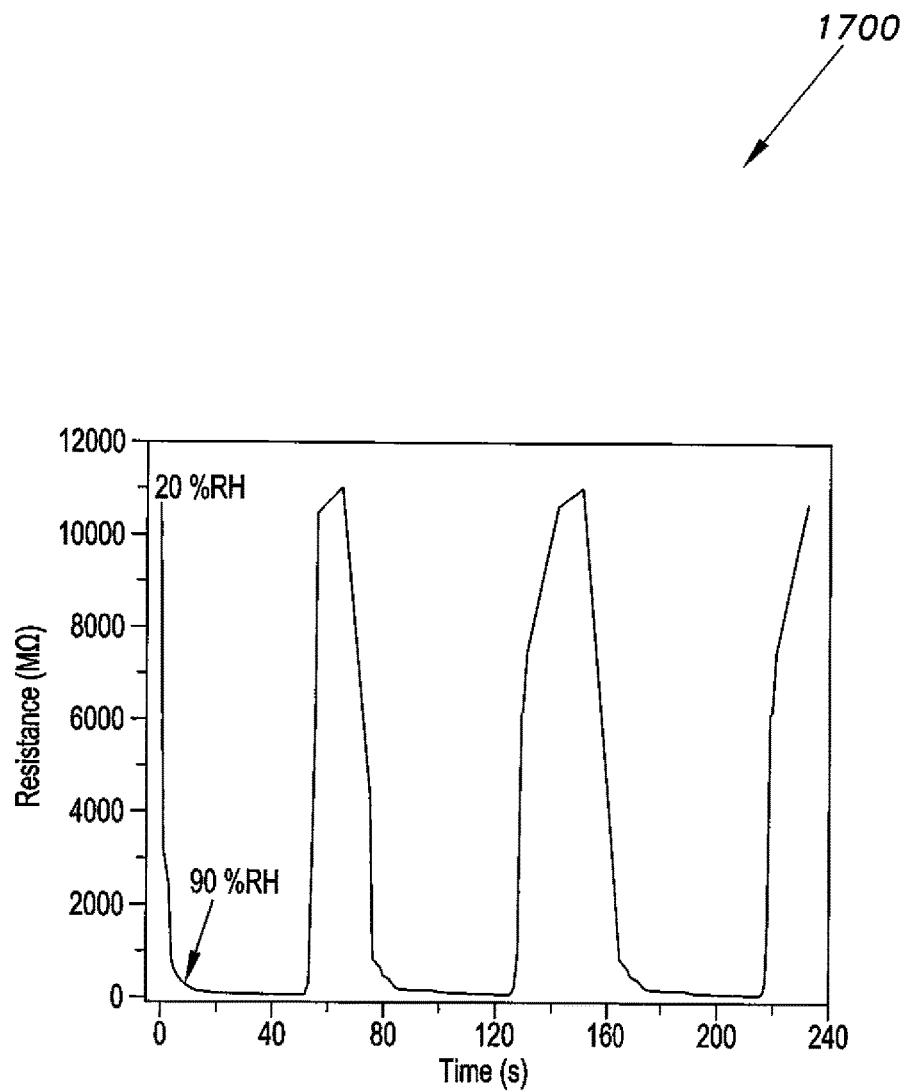
FIG. 17 is a plot showing response and recovery times of the NiPc-GO nanocomposite based sensors fabricated by instrument-less technology.

The range of sensitivity is 10% RH to 90% RH. With increase in the thickness of NiPc-GO film, the initial resistance of the sensors decreases (plot 1500 of FIG. 15). As shown in plot 1600 of FIG. 16, the resistance also decreases with increase in frequency at any relative humidity level. The dependence of the resistance on the frequency can be explained by the dependence of dielectric permittivity, mobility of ions (firstly) and electrons (secondly), and transit time charges transfer on the frequency. The response and recovery times of the sensors were measured, and both were found equal to 4 s. Plot 1700 of FIG. 17 represents the response recovery behavior of NiPc-GO sensors, which are comparable to already studied and commercially available humidity sensors.

It was found the humidity sensitivity of the drop-casted NiPc-$C_{60}$ composite films is 42 times larger than that of thermally evaporated films. Normally, with increase in thickness, the initial resistance of the films decreases, but in this study, evaporated thin (50 nm) film has small resistance, as compared to thick (20 μm) drop casted films, which indicates that the films deposited by physical vapor deposition are more compacted than that of drop-casted films.

It is to be understood that the present invention is not limited to the embodiments described above, but encompasses any and all embodiments within the scope of the following claims.

We claim:

1. A method of making thin film humidity sensors, comprising the steps of:
   depositing thin film aluminum electrodes on a clean glass substrate;
   creating a gap between the aluminum electrodes;
   mixing equal weights of nickel phthalocyanine (NiPc) and fullerene ($C_{60}$) to form an NiPc-$C_{60}$ nanocomposite mixture;
   forming a NiPc-$C_{60}$ pellet from the NiPc-$C_{60}$ nanocomposite mixture; and
   depositing a NiPc-$C_{60}$ nanocomposite film to fill the gap between the aluminum electrodes by thermal vapor deposition, the nanocomposite film forming by evaporation from the NiPc-$C_{60}$ pellet.

2. The method of making thin film humidity sensors according to claim 1, further comprising the steps of:
   cleaning the glass substrate prior to the aluminum deposition step by using acetone in an ultrasonic bath for approximately 10 minutes;
   washing the glass substrate with de-ionized water; and
   drying the glass substrate.

3. The method of making thin film humidity sensors according to claim 1, wherein the gap creating step further comprises the steps of:
   masking the grass substrate with copper wire; and
   plasma-cleaning the glass substrate for about 5 minutes in a thermal evaporator, the glass substrate masking and plasma-cleaning steps being performed before the aluminum deposition step.

4. The method of making thin film humidity sensors according to claim 1, wherein the aluminum electrodes depositing step forms electrodes having a thickness of about 50 nm.

5. The method of making thin film humidity sensors according to claim 1, wherein the gap creating step produces a gap between the electrodes of about 40 μm.

6. The method of making thin film humidity sensors according to claim 1, wherein the NiPc-$C_{60}$ depositing step produces thin films of NiPc-$C_{60}$, the thin films having a thickness between 50 and 200 nm deposited onto the gap between the deposited aluminum electrodes.

7. A humidity sensor formed by the method of claim 1.

* * * * *